United States Patent
Takahashi et al.

(10) Patent No.: US 11,127,123 B2
(45) Date of Patent: Sep. 21, 2021

(54) MEDICAL IMAGE PROCESSING DEVICE AND MEDICAL IMAGE PROCESSING METHOD

(71) Applicant: Hitachi, Ltd., Tokyo (JP)

(72) Inventors: Hisashi Takahashi, Tokyo (JP); Taiga Gotou, Tokyo (JP); Koichi Hirokawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 45 days.

(21) Appl. No.: 16/642,674

(22) PCT Filed: Aug. 22, 2018

(86) PCT No.: PCT/JP2018/030965
§ 371 (c)(1),
(2) Date: Feb. 27, 2020

(87) PCT Pub. No.: WO2019/097796
PCT Pub. Date: May 23, 2019

(65) Prior Publication Data
US 2020/0202499 A1    Jun. 25, 2020

(30) Foreign Application Priority Data
Nov. 17, 2017  (JP) .............................. JP2017-221681

(51) Int. Cl.
*G06K 9/00*      (2006.01)
*G06T 5/00*      (2006.01)
(Continued)

(52) U.S. Cl.
CPC .............. *G06T 5/009* (2013.01); *A61B 6/032* (2013.01); *G06T 5/002* (2013.01); *G06T 5/20* (2013.01);
(Continued)

(58) Field of Classification Search
CPC ........... G06T 5/009; G06T 5/002; G06T 5/20; G06T 5/50; G06T 5/004; G06T 5/003;
(Continued)

(56) References Cited

U.S. PATENT DOCUMENTS

| | | | |
|---|---|---|---|
| 6,411,729 B1 * | 6/2002 | Grunkin | G06T 7/0012 378/54 |
| 2009/0052763 A1 * | 2/2009 | Acharyya | G06T 7/13 382/132 |

(Continued)

FOREIGN PATENT DOCUMENTS

| | | |
|---|---|---|
| JP | 61-169971 A | 7/1986 |
| JP | 2001-283215 A | 10/2001 |

(Continued)

OTHER PUBLICATIONS

International Search Report, dated Nov. 6, 2018, which issued during the prosecution of International Application No. PCT/JP2018/030965, which corresponds to the present application.

*Primary Examiner* — Jose L Couso
(74) *Attorney, Agent, or Firm* — Baker Botts L.L.P.

(57) ABSTRACT

A medical image processing device and a corresponding method are provided that can extract and enhance a signal in a medical image. A medical image processing device that applies image processing to a medical image, the device including an acquiring unit that acquires an original image, a first extraction unit that extracts a local bias component image, a creating unit that decomposes a difference image between the original image and the local bias component image into at least two frequency bands and creates a low-frequency component image formed of a component in the lowest frequency band, a second extraction unit that extracts a local bias component low-frequency image that is a local bias component of the low-frequency component image, and a computing unit that multiplies the local bias (Continued)

component low-frequency image by a gain, adds to the local bias component image, and computes a contrast enhanced image.

10 Claims, 14 Drawing Sheets

(51) Int. Cl.
 *A61B 6/03* (2006.01)
 *G06T 5/20* (2006.01)
 *G06T 5/50* (2006.01)
 *G06T 11/00* (2006.01)

(52) U.S. Cl.
 CPC .............. *G06T 5/50* (2013.01); *G06T 11/008* (2013.01); *G06T 2207/10081* (2013.01); *G06T 2207/20182* (2013.01); *G06T 2207/20224* (2013.01); *G06T 2207/30008* (2013.01); *G06T 2207/30061* (2013.01)

(58) Field of Classification Search
 CPC ......... G06T 5/005; G06T 5/10; G06T 11/008; G06T 7/0012; G06T 7/11; G06T 7/30; G06T 7/13; G06T 7/12; G06T 7/0016; G06T 7/0002; G06T 7/248; G06T 7/40; G06T 2207/10081; G06T 2207/20182; G06T 2207/20224; G06T 2207/30008; G06T 2207/30061; G06T 2207/10116; G06T 2207/30004; G06T 2207/10104; G06T 2207/20081; G06T 2207/20216; G06T 2207/20221; G06T 2207/30048; G06T 2207/20192; G06T 2207/20012; G06T 2207/20036; G06T 2207/20208; G06T 2211/40; G06T 2210/41; A61B 6/032; A61B 6/5205; A61B 6/12; A61B 6/00; A61B 6/461; A61B 6/5211; A61B 6/48; A61B 6/52; A61B 6/542; A61B 6/03; A61B 6/484; A61B 6/037; A61B 6/5235; A61B 6/5247; A61B 1/0009; A61B 1/0638; A61B 8/085; G06K 9/3233; G06K 9/40; G06K 9/6223; G06K 9/6247; G06K 9/6249; G06K 9/32; G06K 9/52; G06K 9/527; G06K 9/6267; G06K 9/6277; G06K 9/629; G06K 2009/4695; G06K 2209/053; G16H 30/20; G16H 30/40; G16H 50/20; G06F 19/00; G21K 2207/005

See application file for complete search history.

(56) References Cited

U.S. PATENT DOCUMENTS

| | | | |
|---|---|---|---|
| 2012/0063662 A1 | 3/2012 | Kwon et al. | |
| 2015/0010224 A1 | 1/2015 | Takahashi et al. | |
| 2015/0379711 A1* | 12/2015 | Imai | G06K 9/4604 |
| | | | 382/132 |
| 2017/0039685 A1* | 2/2017 | Goshen | G06T 5/002 |
| 2017/0154413 A1 | 6/2017 | Yu et al. | |
| 2018/0314906 A1* | 11/2018 | Yang | G06K 9/44 |

FOREIGN PATENT DOCUMENTS

| | | |
|---|---|---|
| JP | 2009-054013 A | 3/2009 |
| JP | 6124868 B2 | 5/2017 |
| JP | 2017-094097 A | 6/2017 |

\* cited by examiner

MEDICAL IMAGE PROCESSING DEVICE AND MEDICAL IMAGE PROCESSING METHOD

TECHNICAL FIELD

The present invention relates to a medical image processing device that applies image processing to a medical image obtained by an X-ray CT apparatus, for example, and a medical image processing method, and to a technique that extracts and enhances the signal of a low-contrast structure included in a medical image.

BACKGROUND ART

An X-ray CT apparatus is an apparatus that applies X-rays from the surroundings of an examinee, subjects projection data acquired at a plurality of projection angles to back projection processing, and creates the cross-sectional images of the examinee, so-called reconstruction images. The created reconstruction images are used for diagnosis of the examinee.

The reconstruction image is an image that the degrees of the attenuation of X-rays at positions on the cross-sectional plane of the examinee are imaged. For example, soft tissue having a small attenuation to a large bone having a large attenuation has relatively small pixel values. The absolute value of the difference between the pixel value of a structure in the examinee and the pixel value of the surrounding tissue of the structure is referred to as a contrast. X-rays to be detected have statistical fluctuations, and a reconstruction image includes noise due to fluctuations. Such noise makes a structure whose pixel value is not so different from the pixel value of surrounding tissue, a so-called low-contrast structure, is unclear, and hampers diagnosis.

Therefore, as a technique of improving image quality of reconstruction images, a large number of methods of reducing noise or enhancing a contrast are studied. For example, PTL 1 discloses a method of enhancing the contrast of a structure on the premise of a combined use of a noise reduction technique.

CITATION LIST

Patent Literature

PTL 1: Japanese Patent No. 6124868

SUMMARY OF INVENTION

Technical Problem

However, since the method of PTL 1 is a method that modulates the contrast of a pixel having a large pixel value difference based on the difference of the pixel value between a pixel of interest and surrounding pixels, although the edge of a structure formed of high-frequency components can be enhanced, the method is not suited to enhancing the inside of a low-contrast structure formed of low-frequency components.

Therefore, it is an object of the present invention to provide a medical image processing device and a medical image processing method that can extract and enhance the signal of a low-contrast structure included in a medical image.

Solution to Problem

In order to achieve the object, in the present invention, a local bias component image that is a local bias component in an original image is extracted, a difference image between the original image and the local bias component image is decomposed into frequencies to create a low-frequency component image, a local bias component low-frequency image that is a local bias component in the low-frequency component image is extracted, and added the local bias component low-frequency image multiplied by a gain to the local bias component image, and a contrast enhanced image is computed.

More specifically, the present invention is a medical image processing device that applies image processing to a medical image, the device including an acquiring unit configured to acquire an original image, a first extraction unit configured to extract a local bias component image that is a local bias component in the original image, a creating unit configured to decompose a difference image between the original image and the local bias component image into at least two frequency bands and create a low-frequency component image formed of a component in a lowest frequency band of the decomposed frequency band, a second extraction unit configured to extract a local bias component low-frequency image that is a local bias component of the low-frequency component image, and a computing unit configured to add the local bias component low-frequency image multiplied by a gain to the local bias component image, and compute a contrast enhanced image.

The present invention is a medical image processing method of applying image processing to a medical image, the method including an acquiring step in which an original image is acquired, a first extraction step in which a local bias component image that is a local bias component in the original image is extracted, a creating step in which a difference image between the original image and the local bias component image is decomposed into at least two frequency bands and a low-frequency component image formed of a component in a lowest frequency band of the decomposed frequency bands is created, a second extraction step in which a local bias component low-frequency image that is a local bias component of the low-frequency component image is extracted, and a computing step in which added the local bias component low-frequency image multiplied by a gain to the local bias component image, and a contrast enhanced image is computed.

Advantageous Effects of Invention

According to the present invention, a medical image processing device and a medical image processing method that can extract and enhance the signal of a low-contrast structure included in a medical image can be provided.

DESCRIPTION OF EMBODIMENTS

First Embodiment

In the following, preferred embodiments of a medical image processing device and a medical image processing method according to the present invention will be described with reference to the accompanying drawings. Note that in the following description and the accompanying drawings, components having the same functional configurations are designated with the same reference signs, and the duplicated description is omitted.

Figure 1:
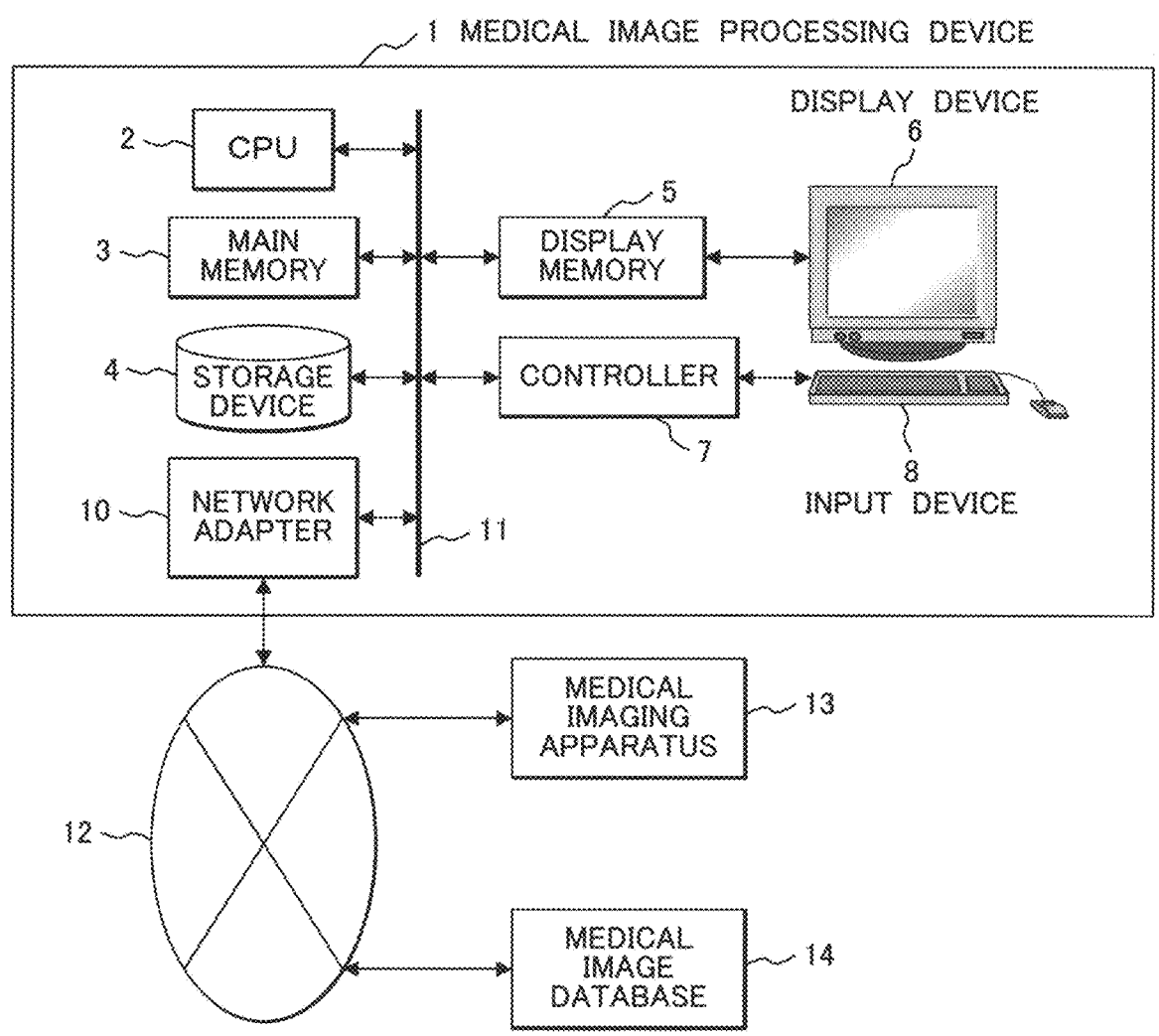
FIG. 1 is a diagram of the overall structure of a medical image processing device 1.

FIG. 1 is a diagram showing the hardware configuration of a medical image processing device 1. The medical image processing device 1 is configured in which a CPU (central Processing Unit) 2, a main memory 3, a storage device 4, a display memory 5, a display device 6, a controller 7, an input device 8, and a network adapter 10 are connected such that signals can be transmitted and received through a system bus 11. The medical image processing device 1 is connected to a medical imaging apparatus 13 and a medical image database 14 via a network 12 such that signals can be transmitted and received. Here, the term "signals can be transmitted and received" means a state in which signals can be mutually transmitted and received or a state in which signals can be transmitted and received from one to the other regardless of electrical, optical, cable, or wireless manners.

The CPU 2 is a device that controls the operation of the components. The CPU 2 loads programs to be stored on the storage device 4 or data necessary to execute the programs to the main memory 3 for execution. The storage device 4 is a device that stores the programs executed by the CPU 2 and the data necessary to execute the programs, specifically a hard disk, for example. Various types of data are transmitted and received via the network 12, such as a LAN (Local Area Network). The main memory 3 is a memory that stores the programs executed by the CPU 2 and arithmetic operation processes in progress.

The display memory 5 is a memory that temporarily stores display data to be displayed on the display device 6, such as a liquid crystal display. The input device 8 is an operation device that instructs the medical image processing device 1 to operate by an operator, and specifically, is a keyboard, and a mouse, and any other device. The mouse maybe a pointing device, such as a track pad, a track ball, and any other device. The controller 7 is a device that detects the state of the mouse, acquires the position of a mouse pointer on the display device 6, and outputs acquired positional information, for example, to the CPU 2. The network adapter 10 is a device that connects the medical image processing device 1 to the network 12, such as a LAN, a telephone line, the Internet, and any other network.

The medical imaging apparatus 13 is an apparatus that acquires medical images such as the cross-sectional images of an examinee. The medical imaging apparatus 13 is an X-ray CT apparatus, for example, and will be described later using FIG. 2. The medical image database 14 is a database system that stores medical images acquired by the medical imaging apparatus 13.

Figure 2:
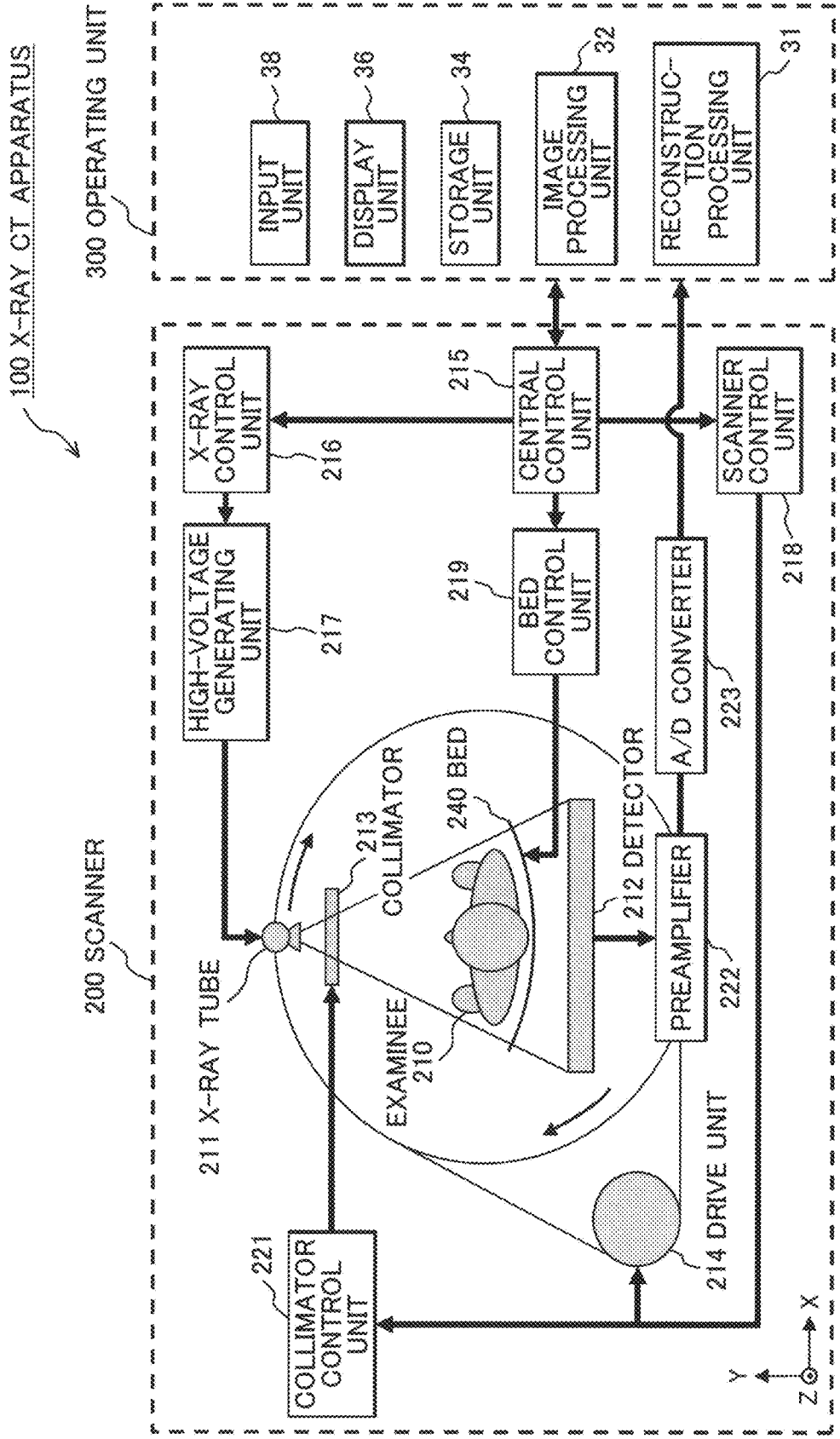
FIG. 2 is a diagram of the overall structure of an X-ray CT apparatus 100 that is an example of a medical imaging apparatus 13.

The overall structure of the X-ray CT apparatus 100 that is an example of the medical imaging apparatus 13 will be described using FIG. 2. Note that in FIG. 2, the lateral direction is an X-axis, the vertical direction is a Y-axis, and a direction perpendicular to the paper surface is a Z-axis. The X-ray CT apparatus 100 includes a scanner 200 and an operating unit 300. The scanner 200 has an X-ray tube 211, a detector 212, a collimator 213, a drive unit 214, a central control unit 215, an X-ray control unit 216, a high-voltage generating unit 217, a scanner control unit 218, a bed control unit 219, a collimator control unit 221, a preamplifier 222, an A/D converter 223, a bed 240, and the like.

The X-ray tube 211 is a device that applies X-rays to an examinee 210 placed on the bed 240. By the application of a high voltage generated by the high-voltage generating unit 217 according to a control signal transmitted from the X-ray control unit 216 to the X-ray tube 211, X-rays are applied from the X-ray tube 211 to the examinee.

The collimator 213 is a device that restricts the application range of X-rays applied from the X-ray tube 211. The application range of X-rays is set according to a control signal transmitted from the collimator control unit 221.

The detector 212 is a device that detects X-rays transmitted through the examinee 210 and measures spatial distribution of the X-rays. The detector 212 is disposed opposite to the X-ray tube 211, and a large number of detection elements are two-dimensionally arranged inside a plane opposite to the X-ray tube 211. The signal measured at the detector 212 is amplified at the preamplifier 222, and then converted into a digital signal at the A/D converter 223. After that, various correction processes are applied to the digital signal, and projection data is acquired.

The drive unit 214 rotates the X-ray tube 211 and the detector 212 around the examinee 210 according to a control signal transmitted from the scanner control unit 218. By the application and detection of X-rays together with the rotation of the X-ray tube 211 and the detector 212, projection data at a plurality of projection angles is acquired. The data collection unit for every projection angle is referred to as a view. In the arrangement of the two-dimensionally arranged detection elements of the detector 212, the rotation direction of the detector 212 is referred to as a channel, and a direction orthogonal to the channel is referred to as a column. The projection data is identified by the view, the channel, and the column.

The bed control unit 219 controls the operation of the bed 240, and keeps the bed 240 stationary or moves the bed 240 in the Z-axis direction at constant velocity during the application and detection of X-rays. The scan in which the bed 240 is kept stationary is referred to as axial scan, and the scan in which the bed 240 is being moved is referred to as helical scan.

The central control unit 215 controls the operation of the scanner 200 described above according to instructions from the operating unit 300. Next, the operating unit 300 will be described. The operating unit 300 has a reconstruction processing unit 31, an image processing unit 32, a storage unit 34, a display unit 36, an input unit 38, and the like.

The reconstruction processing unit 31 creates a reconstruction image by subjecting the projection data acquired by the scanner 200 to back projection processing. The image processing unit 32 performs various image processes in order to make the reconstruction image an image suited to diagnosis. The storage unit 34 stores projection data, reconstruction images, and processed images. The display unit 36 displays reconstruction images and processed images. The input unit 38 is used when the operator sets the acquisition conditions of projection data (tube voltages, tube electric currents, scan speed, and any other parameter) and the reconstruction conditions of a reconstruction image (a reconstruction filter, an FOV size, and any other parameter).

Note that the operating unit 300 may be the medical image processing device 1 shown in FIG. 1. In this case the image processing unit 32 corresponds to the CPU 2, the storage unit 34 corresponds to the storage device 4, the display unit 36 corresponds to the display device 6, and the input unit 38 corresponds to the input device 8.

Figure 3:
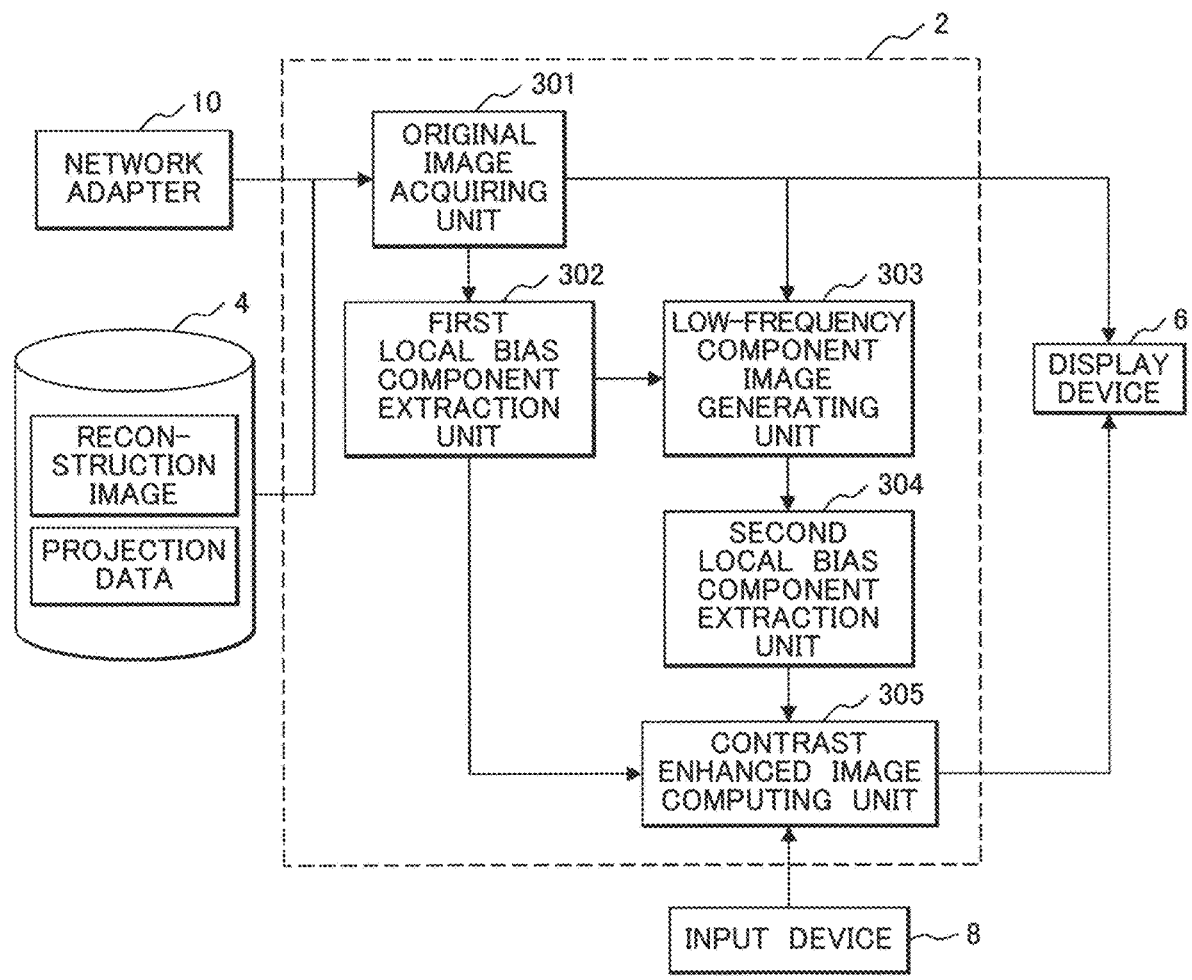
FIG. 3 is a functional block diagram of a first embodiment.

The main components of the embodiment will be described using FIG. 3. Note that these main components may be configured of dedicated hardware, or may be configured of software operated on the CPU 2. In the following description, the case will be described in which the main components of the embodiment are configured of software.

The embodiment includes an original image acquiring unit 301, a first local bias component extraction unit 302, a low-frequency component image creating unit 303, a second local bias component extraction unit 304, and a contrast enhanced image computing unit 305. On the storage device 4, reconstruction images created in the X-ray CT apparatus 100 and projection data are stored. In the following, the component units will be described.

The original image acquiring unit 301 acquires an original image that is a target for image processing. The original image may be a reconstruction image stored on the storage device 4, or may be a reconstruction image acquired from the medical imaging apparatus 13 or the medical image database 14 through the network adapter 10. A configuration may be provided in which the original image acquiring unit 301 acquires projection data from the storage device 4, the medical imaging apparatus 13, or the medical image database 14, creates a reconstruction image from the acquired projection data, and acquires the created reconstruction image as an original image.

The first local bias component extraction unit 302 extracts a local bias component in the reconstruction image that is an original image, and creates a local bias component image. The local bias component image is an image in which a pixel having a difference between the pixel value of a pixel in proximity to a target pixel and the pixel value of the target pixel is smaller than a predetermined threshold is grouped, and the pixel value of the pixel in the group is replaced with a representative value. In many cases, the mean value of the pixel values of the pixels in the group are used for the representative value.

FIG. 4 shows an example of a local bias component image together with a reconstruction image that is an original image. FIG. 4(a) shows a reconstruction image, and FIG. 4(b) shows a local bias component image. FIG. 4(c) shows examples of profiles of pixel values on both images, and FIG. 4(d) shows the appearance of a phantom used for creating the reconstruction image. The phantom shown in FIG. 4(d) is a phantom that a low-contrast structure having a CT value close to the CT value of water is arranged on concentric circles in water. The low-contrast structures have columnar shapes having different outer diameters and lengths.

Figure 4A:
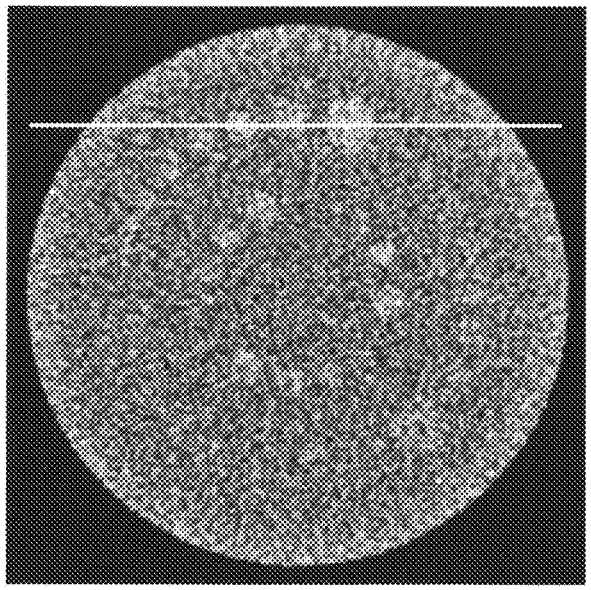
FIGS. 4(a)-4(d) are diagrams showing examples of local bias component images.
Figure 4B:
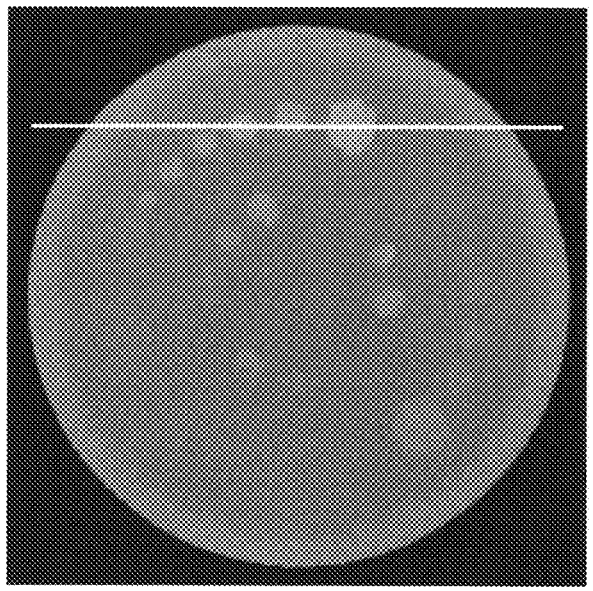
Figure 4C:
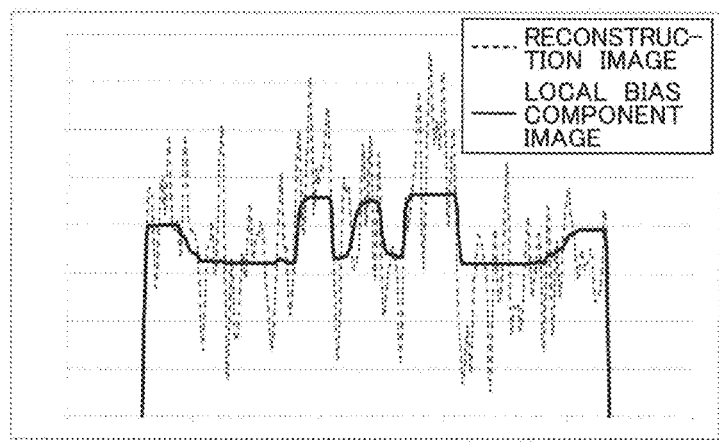
Figure 4D:
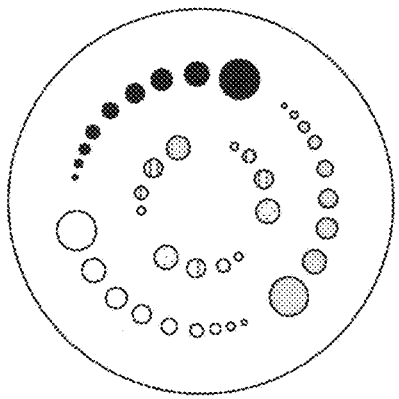

From the comparison of two profiles in FIG. 4(c), the local bias component image is an image from which fine fluctuation components in the reconstruction image are removed and is regarded as an image showing the outside shape of the low-contrast structure. That is, the image that images the local bias component in the reconstruction image is the local bias component image. Note that although noise is reduced from the local bias component image, fine fluctuation components in the low-contrast structure are also removed, and the local bias component image is not suited to diagnosis.

Figure 5A:
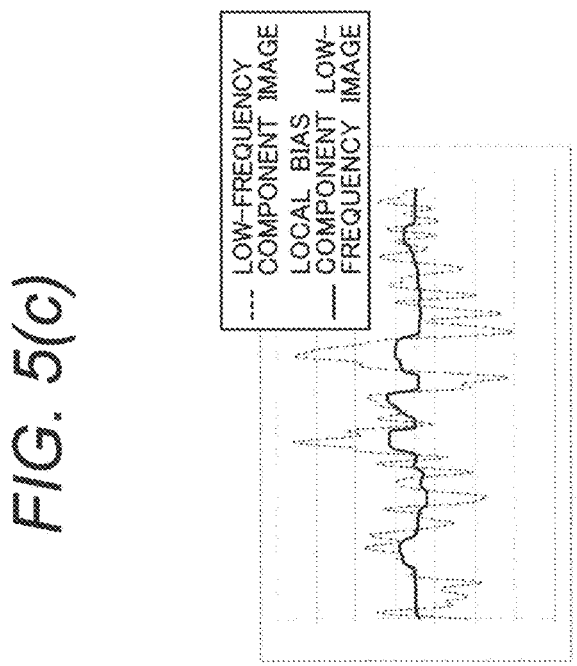
FIGS. 5(a)-5(c) are diagrams showing an example of a low-frequency component image and an example of a local bias component low-frequency image.

The low-frequency component image creating unit 303 decomposes a difference image between the reconstruction image that is an original image and the local bias component image into a plurality of frequency bands, and creates a low-frequency component image formed of a component in the lowest frequency band of the decomposed frequency band. Since the local bias component image is regarded as an image showing the outside shape of a structure, the difference image between the reconstruction image and the local bias component image is an image showing fine fluctuation components in the reconstruction image. From diagnosis, since useful information is low-frequency components showing the inside of a low-contrast structure, here, a difference image is decomposed into frequencies, and a low-frequency component image formed of low-frequency components is created. An example of the low-frequency component image is shown in FIG. 5(a). Note that a cutoff frequency for use in performing frequency decomposition is appropriately set suitable for a diagnostic purpose.

The second local bias component extraction unit 304 extracts local bias components in the low-frequency component image, and creates a local bias component low-frequency image. Although the input image is different between the reconstruction image and the low-frequency component image, the process of extracting local bias components in the input image is the same as the process by the first local bias component extraction unit 302.

Figure 5B:
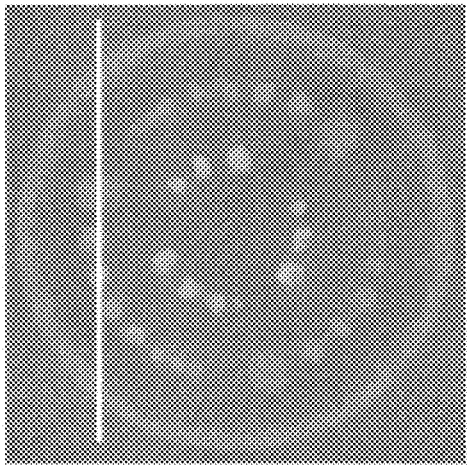
Figure 5C:
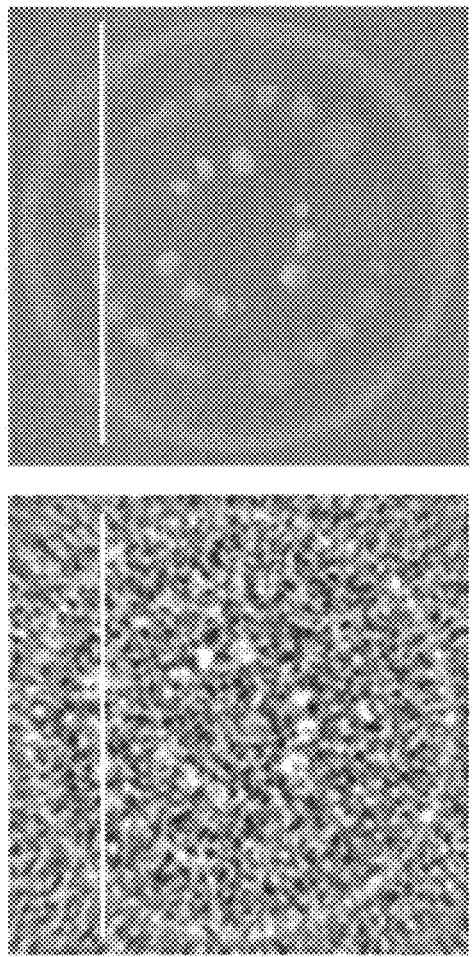

An example of the local bias component low-frequency image is shown in FIG. 5(b). FIG. 5(c) shows examples of profiles of pixel values on both of the low-frequency component image and the local bias component low-frequency image. From the comparison of two profiles in FIG. 5(c), the local bias component low-frequency image is regarded as an image from which noise of the low-frequency component image is removed.

The contrast enhanced image computing unit 305 multiplies the local bias component low-frequency image by a signal enhancement gain, adds to the local bias component image, and computes a contrast enhanced image. When the local bias component image is I1, the local bias component low-frequency image is I2, and the signal enhancement gain is g, a contrast enhanced image I is expressed by the following expression.

$$I = I1 + g \times I2 \qquad \text{[Expression 1]}$$

Since the local bias component image I1 is an image showing the outside shape of the low-contrast structure and the local bias component low-frequency image I2 is an image in which noise is removed from an image showing low-frequency components showing the inside of the low-contrast structure, the contrast enhanced image I obtained by adding both images is an image suited to diagnosis of a low-contrast structure. The signal enhancement gain g is adjusted according to a diagnostic purpose, and the contrast enhanced image I is an image more suited to diagnosis.

Figure 6:
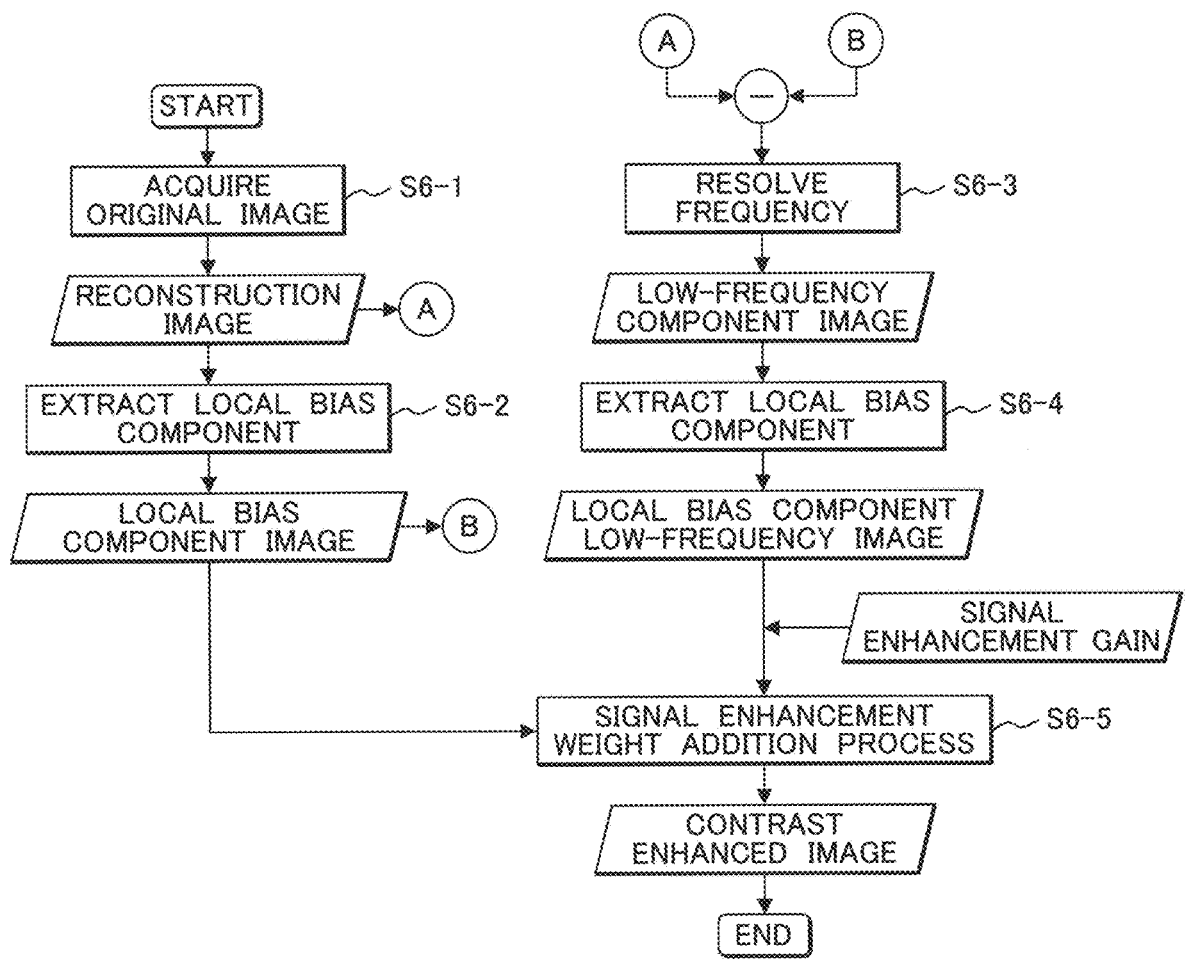
FIG. 6 is a diagram showing a process flow according to the first embodiment.

A process flow executed by the medical image processing device 1 including the component unit described above will be described using FIG. 6.

(S6-1)

The original image acquiring unit 301 acquires a reconstruction image as an original image. The reconstruction image may be acquired from the storage device 4, or may be acquired from the medical imaging apparatus 13 or the medical image database 14 through the network adapter 10. A reconstruction image created from projection data acquired from the storage device 4, the medical imaging apparatus 13, or the medical image database 14 may be acquired as an original image.

(S6-2)

The first local bias component extraction unit 302 extracts local bias components in the reconstruction image, and creates a local bias component image. For creating a local bias component image, a Total Variation (TV) filter or a Non-Local Means (NLM) filter, for example, may be used.

First, an example of using a TV filter will be described. When the pixel number of the reconstruction image is set to J, the index of a pixel is set to j, and the j-th pixel value of the pixel is set to $x_j$, the pixel value of the reconstruction image can be set to the J-dimensional vector $x=\{x_1, \ldots, x_j, \ldots, x_J\}$. An image z obtained by the application of the TV filter is expressed by the following expression.

$$z = \underset{y}{\mathrm{argmin}} \left\{ \frac{1}{2} \|x - y\|_D^2 + \beta \|y\|_{TV} \right\}$$ [Expression 2]

Here, y is a J-dimensional variable vector for computation, and D is a J×J diagonal matrix that has a weighting factor relating to a data fidelity term on a diagonal component. D may be a unit matrix. $\|x-y\|_D^2 = (x-y)^T D(x-y)$. The right-hand side first term operates such that the image z to be obtained is not apart from the original image x so much. $\|\cdot\|_{TV}$ is a TV norm. The right-hand side second term operates such that excessive vibrational components in the image z to be obtained are suppressed. In other words, the first term and the second term have reverse actions to each other. γ is a given parameter that is zero or more, and is used for adjusting the balance between the first term and the second term.

In Expression 2, since β is included in the second term, the influence of the second term is more increased as β is greater, and the smoothing effect is improved. When the smoothing effect is improved too much, the image z to be obtained is blurred, whereas when β is too small, the smoothing effect is insufficient. For example, in the case where let β=0, the image z to be obtained remains as the original image x, and no smoothing is achieved at all. β is desirably set to an appropriate value corresponding to noise included in the original image x. Here, β is computed based on Expression 2 such that a phantom having a known pixel value and including a uniform region, e.g. a phantom in a cylindrical shape filled with water, for example, is scanned to create a reconstruction image and the created reconstruction image x is a smoothed image z suited to diagnosis.

Note that since noise included in the reconstruction image x is varied depending on the size of the phantom or the scan conditions, the value of β is computed for each of the size of the phantom or the scan conditions, the association of the values of β with these conditions is stored on the storage device 4. In the execution of this step after storing the association, the value of β corresponding to the corresponding scan conditions or the size of the examinee 210 is read from the storage device 4 for use in Expression 2. For example, in the case where the tube voltage that is one of the scan conditions includes four types of 80, 100, 120, and 140 kV, suitable β corresponding to the tube voltages is computed in advance and stored on the storage device 4. When the tube voltage is 120 kV in acquiring a reconstruction image, β corresponding to 120 kV is read and used.

Next, the NLM filter an example of using will be described. When the pixel value of the reconstruction image is set to the J-dimensional vector $x=\{x_1, \ldots, x_k, \ldots, x_J\}$, an image $y_j$ obtained by the application of the NLM filter is expressed by the following expression.

$$y_j = \Sigma_{k \in J} w_{j,k} x_k \forall j$$ [Expression 3]

Here, $w_{j,k}$ is expressed by the following expression.

$$w_{j,k} = \frac{1}{z_j} e^{-\frac{\|u_j - u_k\|_{2,a}^2}{h^2}}$$ [Expression 4]

$z_j$ is expressed by the following expression.

$$z_j = \sum_{k \in J} e^{-\frac{\|u_j - u_k\|_{2,a}^2}{h^2}}$$ [Expression 5]

Note that $u_j$ is a vector having an element that is the pixel value of the pixel included in a rectangular kernel with the j-th pixel as the center, and a is the standard deviation of a Gaussian kernel. h is a given parameter and has the operation similar to β of the TV filter, the setting method and the use method are similar to β, and the detailed description is omitted. Note that the size of the rectangular kernel can be freely set, and a kernel in a degree of a 7×7 size, for example, is used as a constant.

(S6-3)

The low-frequency component image creating unit 303 decomposes a difference image between the reconstruction image and the local bias component image into frequencies, and creates a low-frequency component image. For frequency decomposition, methods, such as a decomposition method using a Gaussian pyramid or a Fourier transform in a real space, can be used. In the case where a Gaussian pyramid is used, a Gaussian filter in which the cutoff frequency is set to 0.15 lp/mm, for example, is applied to the difference image, and a low-frequency component image is created.

(S6-4)

The second local bias component extraction unit 304 extracts a local bias component low-frequency image from the low-frequency component image. Although the local bias component extraction process is similar to S6-2, values different from the values in S6-2 are used for β of the TV filter or h of the NLM filter. This is because although the input in S6-2 is the reconstruction image, the input in the present step is the low-frequency component image, and the size of fluctuations in the pixel value is different between these two images. However, since the requirement for β or h is similar to the requirement in S6-2, in the procedures described in S6-2, the input image is replaced by the low-frequency component image from the reconstruction image, and then an appropriate β or h is computed in advance, and stored on the storage device 4 for use.

(S6-5)

The contrast enhanced image computing unit 305 computes a contrast enhanced image. For computing the contrast enhanced image, Expression 1 is used. The computed contrast enhanced image is displayed on the display device 6.

Figure 7:
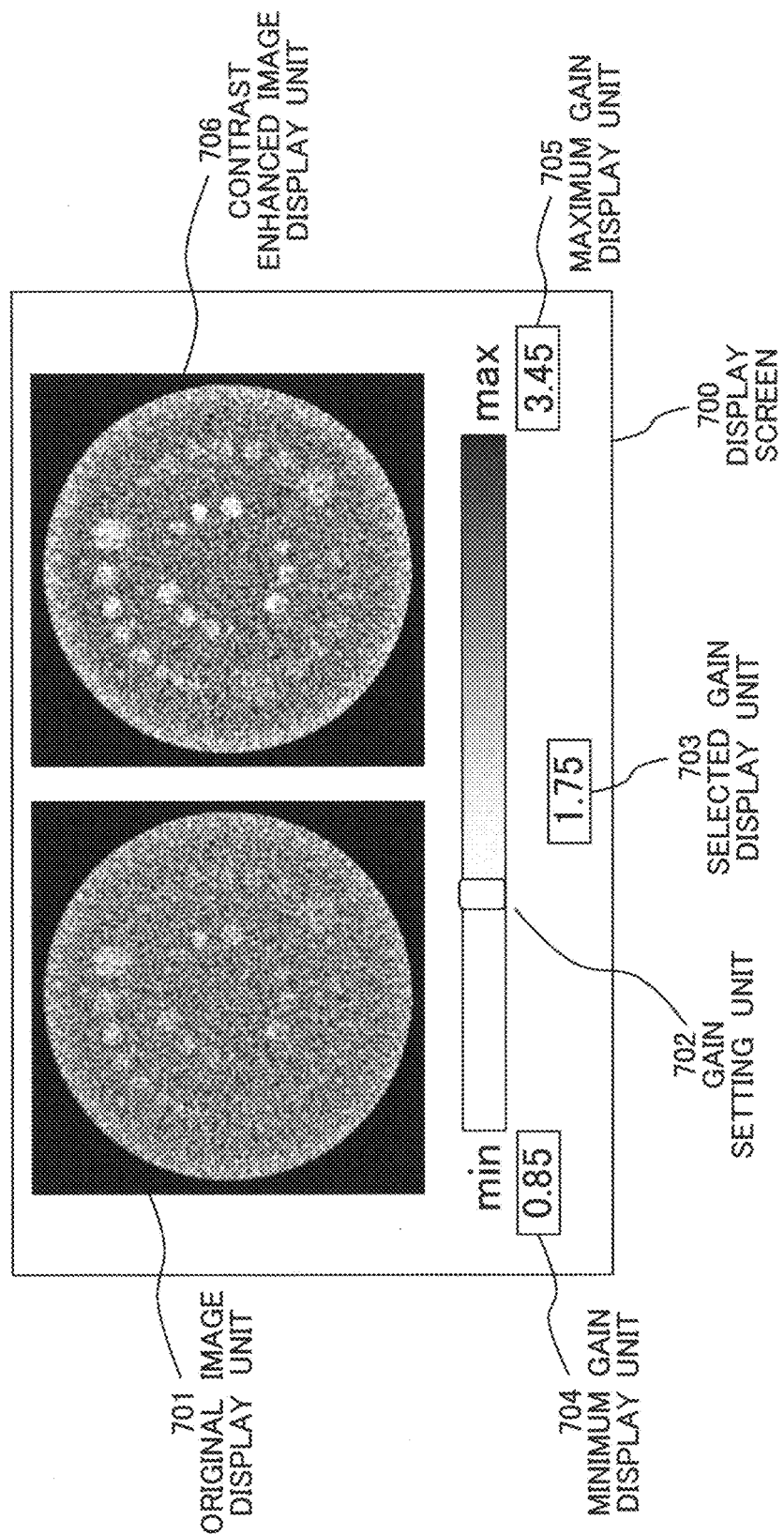
FIG. 7 is a diagram showing an example of a display screen according to the first embodiment.

FIG. 7 shows an example of a display screen 700. The display screen 700 has an original image display unit 701, a gain setting unit 702, a selected gain display unit 703, a minimum gain display unit 704, a maximum gain display unit 705, and a contrast enhanced image display unit 706. In the following, these components will be described.

On the original image display unit 701, an original image such as a reconstruction image is displayed. The gain setting unit 702 is a slider used for setting the signal enhancement gain. The operator horizontally moves the gain setting unit 702 using a mouse, for example, and the value of the signal enhancement gain is changed. On the selected gain display unit 703, the value of the set signal enhancement gain is displayed. The operator can confirm the value of the signal enhancement gain from the numerical value of the selected gain display unit 703.

On the minimum gain display unit 704 and the maximum gain display unit 705, the settable minimum value and maximum value of the signal enhancement gain are displayed. The settable minimum value and maximum value of the signal enhancement gain are computed corresponding to the reconstruction conditions, for example. For example, in the case where a lung field reconstruction filter is selected, noise on the reconstruction image and noise on the contrast enhanced image are prone to be increased, compared with the case where an abdominal reconstruction filter is selected. Therefore, the range of the signal enhancement gain for the lung field reconstruction filter may be set wider than in the abdominal reconstruction filter.

On the contrast enhanced image display unit 706, the computed contrast enhanced image, i.e., the result of image processing is displayed. The contrast enhanced image is updated every time the value of the signal enhancement gain is changed. The operator who operates the display screen 700 sets the value of the signal enhancement gain using the gain setting unit 702, and the contrast enhanced image to be computed can be interactively displayed.

Figure 8:
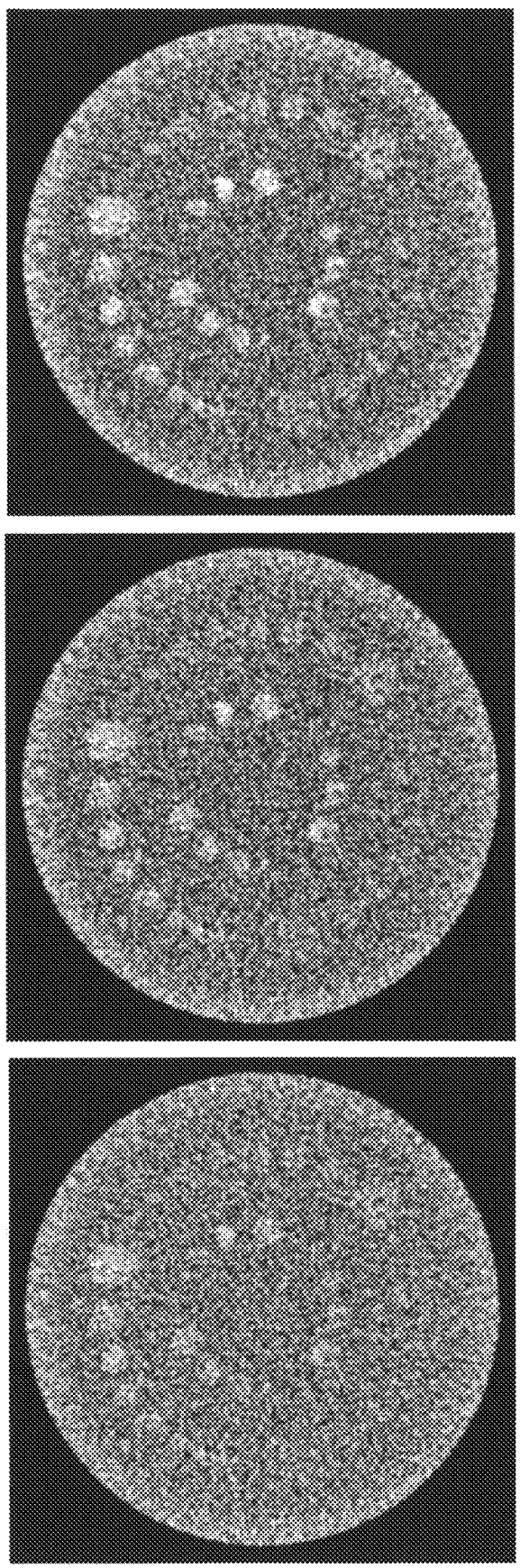
FIGS. 8(a)-8(c) are diagrams showing examples of contrast enhanced images having different gains.

FIG. 8 shows examples of contrast enhanced images in the case where different signal enhancement gains are set together with a reconstruction image. FIG. 8(*a*) shows a reconstruction image, FIG. 8(*b*) shows a contrast enhanced image in the case where the signal enhancement gain is made relatively small, and FIG. 8(*c*) shows a contrast enhanced image in the case where the signal enhancement gain is made relatively large. It is found that changing the signal enhancement gain varies the ways to see the low-contrast structure.

From the process flow described above, the signal of a low-contrast structure included in a medical image can be extracted and enhanced, and a medical image suited to diagnosis can be present to the operator.

Second Embodiment

In the first embodiment, the description is made in which the local bias component low-frequency image is weight-added to the local bias component image to compute a contrast enhanced image. In order to obtain more detailed information, desirably, the low-frequency component image as well as other frequency components are reflected on the contrast enhanced image. Therefore, in the embodiment, a contrast enhanced image in which other frequency components are reflected together with a low-frequency component will be described.

Figure 9:
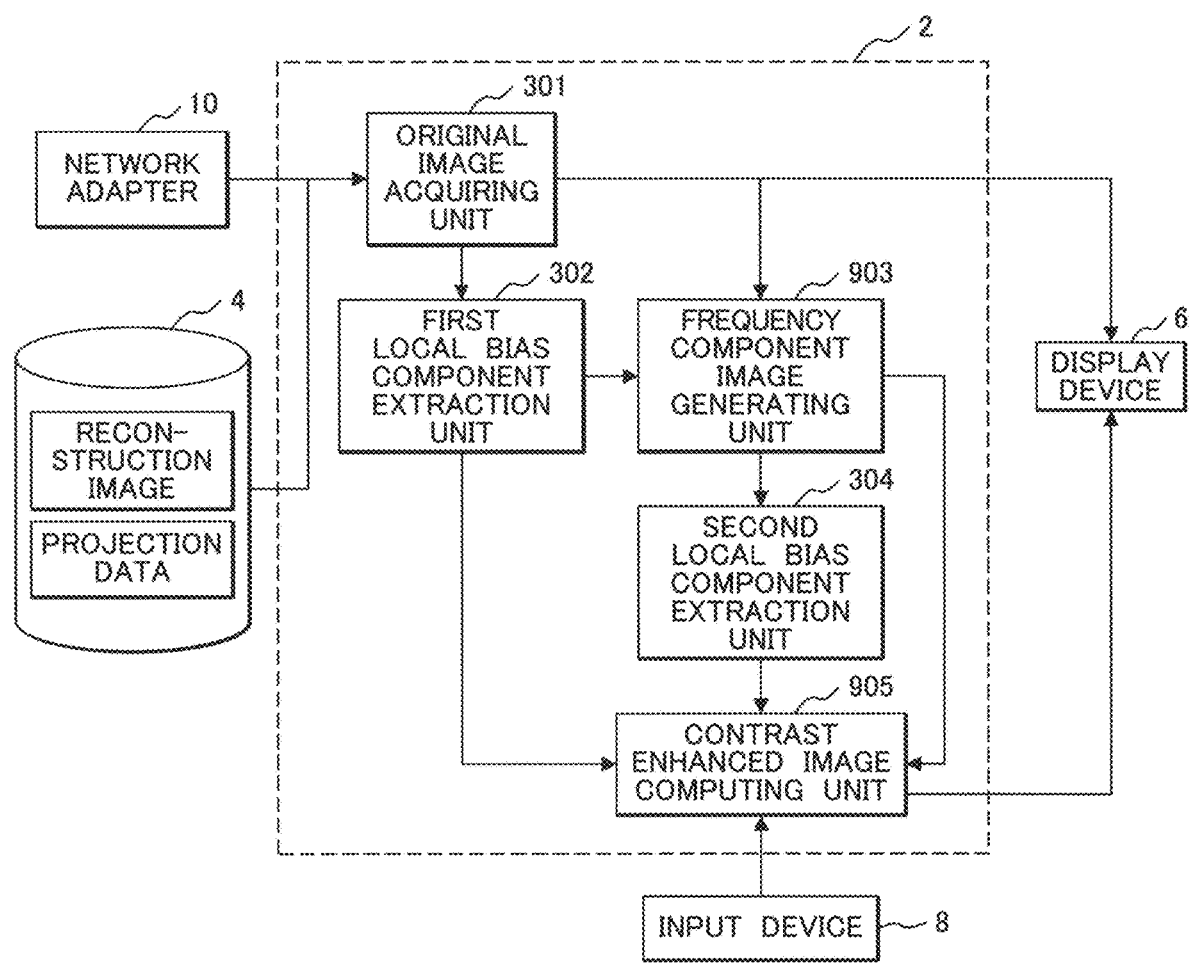
FIG. 9 is a functional block diagram of a second embodiment.

The main components of the embodiment will be described using FIG. 9. Note that since the difference between the embodiment and the first embodiment is that the low-frequency component image creating unit 303 according to the first embodiment is changed to a frequency component image creating unit 903 and the difference is the content of processes in a contrast enhanced image computing unit, the frequency component image creating unit 903 and a contrast enhanced image computing unit 905 will be described.

The frequency component image creating unit 903 decomposes a difference image between a reconstruction image that is an original image and a local bias component image into a plurality of frequency bands. Computing the difference image between the reconstruction image and the local bias component image and decomposing the difference image into a plurality of frequency bands to create a low-frequency component image are the same as in the low-frequency component image creating unit 303 according to the first embodiment. In the frequency component image creating unit 903, another frequency component image that is a frequency component image formed of a component in a frequency band different from the low-frequency component image is created.

In order to create the other frequency component image, frequency decomposition is performed using a cutoff frequency different from the cutoff frequency used by the low-frequency component image creating unit 303, or a low-frequency component image is differenced from the difference image between the reconstruction image and the local bias component image. The other frequency component image is not limited to one image as long as the other frequency component image is a frequency component image of components in a frequency band different from the low-frequency component image, and a plurality of other frequency component images may be created. The created other frequency component image is transmitted to the contrast enhanced image computing unit 905.

The contrast enhanced image computing unit 905 multiplies a local bias component low-frequency image by a signal enhancement gain to add to the other frequency component image together with the local bias component image, and computes a contrast enhanced image. When the local bias component image is set to I1, the local bias component low-frequency image is I2, the other frequency component image is I3, and the signal enhancement gain is g, and a contrast enhanced image I is expressed by the following expression.

$$I = I1 + g \times I2 + I3 \qquad \text{[Expression 6]}$$

Since a local bias component low-frequency image I2 is weight-added to a local bias component image I1 and the other frequency component image I3 is added, the contrast enhanced image I in which detailed information is further reflected is an image more suited to diagnosis.

Figure 10:
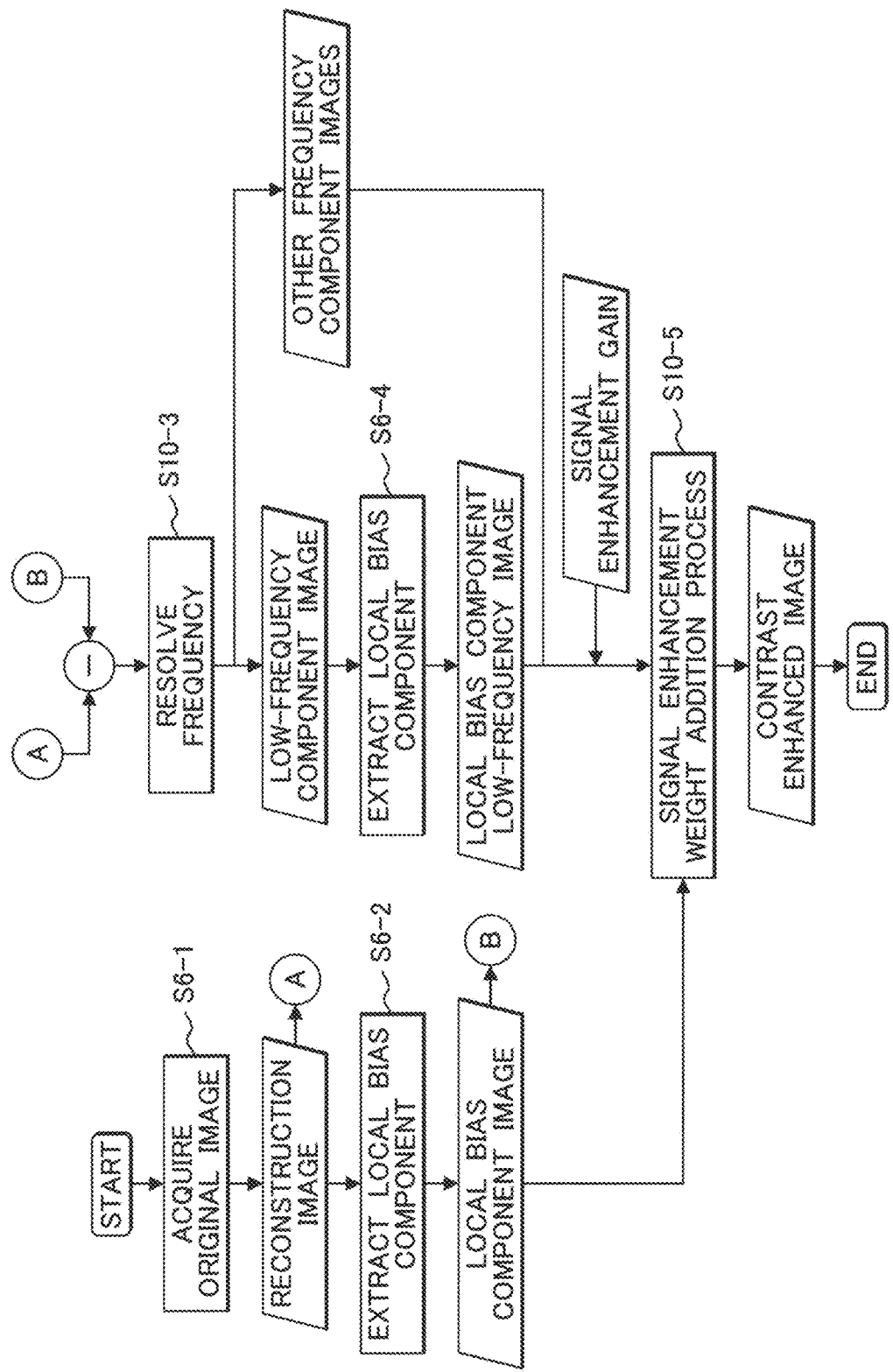
FIG. 10 is a diagram showing a process flow according to the second embodiment.

Referring to FIG. 10, a process flow executed by a medical image processing device 1 according to the embodiment will be described. Note that S6-1, S6-2, and S6-4 in the embodiment are the same as the first embodiment, and the description is omitted.

(S10-3)

The frequency component image creating unit 903 decomposes a difference image between a reconstruction image and a local bias component image into frequencies, and creates a low-frequency component image and another frequency component image. In the case where a Gaussian pyramid is used for frequency decomposition, a Gaussian filter in which the cutoff frequency is set to 0.15 lp/mm, for example, is applied to the difference image, a low-frequency component image is created, the low-frequency component image is differenced from the difference image, and then the other frequency component image is created.

(S10-5)

The contrast enhanced image computing unit 905 computes a contrast enhanced image. For computing the contrast enhanced image, Expression 6 is used. The computed contrast enhanced image is displayed on a display device 6.

From the process flow described above, the signal of a low-contrast structure included in a medical image is extracted and enhanced, the detailed information can be reflected, and a medical image more suited to diagnosis can be present to an operator.

Third Embodiment

In the first embodiment, the description is made in which the fluctuation components of the pixel values in the reconstruction image and the low-frequency component image are removed to extract a local bias component. Although most of the fluctuation component of the pixel value is a noise component, components relating to a structure in an examinee are also included. Thus, in removing the fluctuation component, using a noise map showing the distribution of noise components can improve the extraction accuracy of bias components. Therefore, in the embodiment, the extraction of local bias components from a reconstruction image and a low-frequency component image using a noise map will be described.

Figure 11:
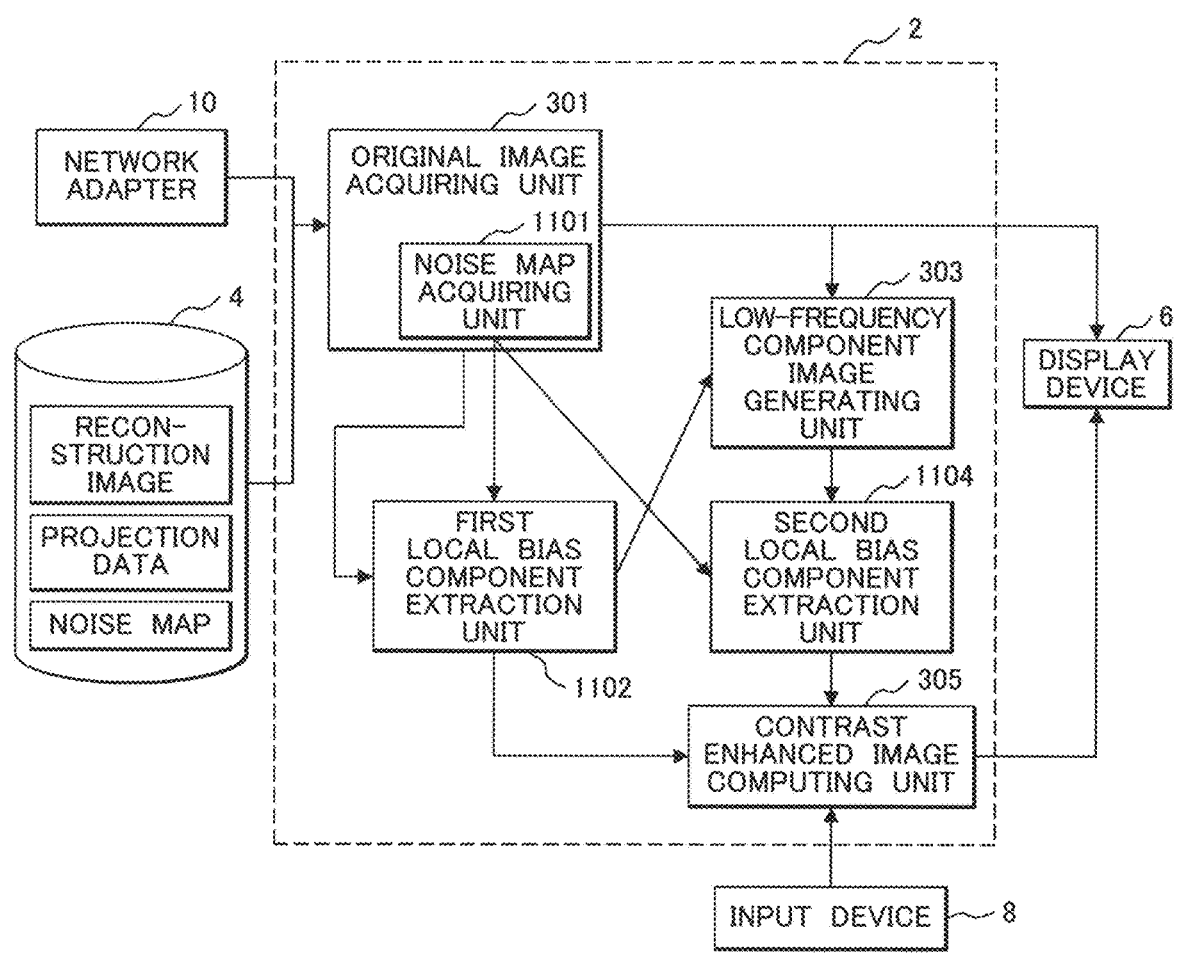
FIG. 11 is a functional block diagram of a third embodiment.

The main components of the embodiment will be described using FIG. 11. Note that the difference between the embodiment and the first embodiment is that the original image acquiring unit 301 according to the first embodiment includes a noise map acquiring unit 1101 and that a first local bias component extraction unit and a second extraction unit use a noise map. In the following, the noise map acquiring unit 1101, the first local bias component extraction unit 1102, and the second extraction unit 1104 will be described.

The noise map acquiring unit 1101 acquires a noise map on which the distribution of noise components in a reconstruction image that is an original image is imaged. The noise map is stored on a storage device 4, a medical imaging apparatus 13, or a medical image database 14, and is read from these devices. The noise map acquiring unit 1101 may create a noise map using projection data used for creating a reconstruction image. The projection data used for creating a noise map is read from the storage device 4, the medical imaging apparatus 13, or the medical image database 14. The acquired noise map is transmitted to the first local bias component extraction unit 1102 and the second extraction unit 1104. Note that FIG. 11 shows a form in which the noise map acquiring unit 1101 is included in an original image acquiring unit 301. However, it is acceptable that the noise map acquiring unit 1101 is not included in the original image acquiring unit 301.

The first local bias component extraction unit 1102 extracts local bias components in the reconstruction image that is an original image using the noise map, and creates a local bias component image. Similarly to the first embodiment, the created local bias component image is transmitted to a low-frequency component image creating unit 303 and a contrast enhanced image computing unit 305.

The second local bias component extraction unit 1104 extracts local bias components in a low-frequency component image using the noise map, and creates a local bias component low-frequency image. Similarly to the first embodiment, the created local bias component low-frequency image is transmitted to the contrast enhanced image computing unit 305.

Figure 12:
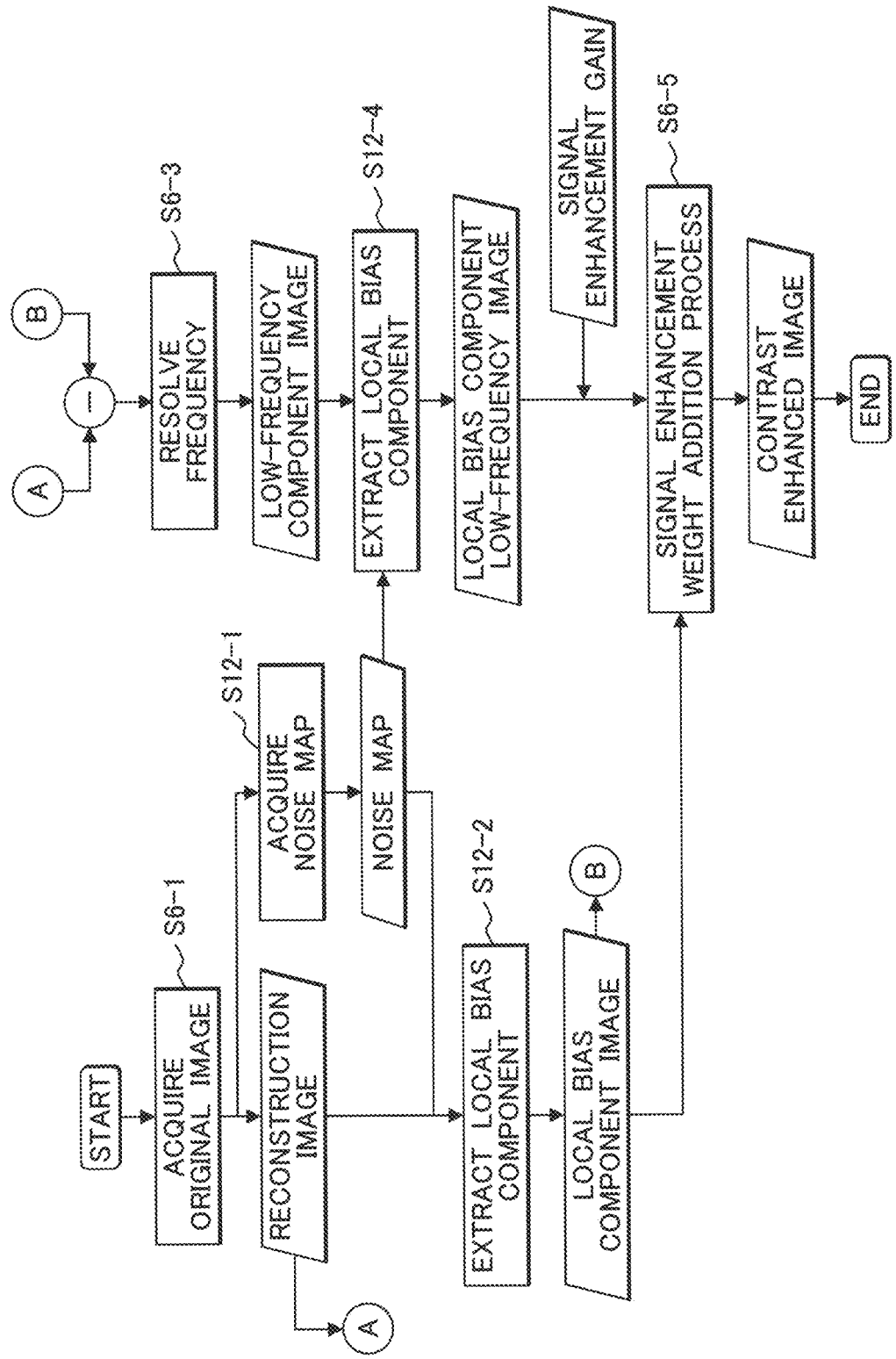
FIG. 12 is a diagram showing a process flow according to the third embodiment.

Referring to FIG. 12, a process flow executed by a medical image processing device 1 according to the embodiment will be described. Note that S6-1, S6-3, and S6-5 in the embodiment are the same as the first embodiment, and the description is omitted.

(S12-1)

The noise map acquiring unit 1101 acquires a noise map. In the following, an example of procedures of creating a noise map by the noise map acquiring unit 1101 will be described. First, projection data used for creating the reconstruction image is acquired. Subsequently, the projection data is separated into even-numbered views and odd-numbered views, and a reconstruction image for every item of the separated projection data is created. The other of two reconstruction images is subtracted from one of two reconstruction images, a structure is removed, and an image on which noise components are reflected is acquired. Note that adding the two reconstruction images makes a reconstruction image created using all items of the projection data. Finally, standard deviation is computed to the pixels in the image on which noise components are reflected using the pixel values of a target pixel and the neighboring pixels of the target pixel, and the values of the standard deviation computed to the pixels are formed into a noise map.

(S12-2)

The first local bias component extraction unit 1102 extracts local bias components in the reconstruction image using the noise map, and creates a local bias component image. Similarly to the first embodiment, for creating the local bias component image, the TV filter or the NLM filter can be used.

In the case where the noise map is used for the TV filter, the reciprocal of the value of the noise map is fit into the diagonal component of the diagonal matrix D in Expression 2. Specifically, when the value of the j-th pixel in the noise map is set to $n_j$, $D=\text{diag}\{1/n_1, \ldots, 1/n_j, \ldots, 1/n_J\}$ is expressed. Similarly to S6-2 according to the first embodiment, an appropriate β is computed in advance for each of the scan conditions using this matrix D, and stored on a storage device.

In the case where the noise map is used for the NLM filter, the parameter h of Expression 4 is replaced by the J-dimensional vector $h=\{h_1, \ldots, h_j, \ldots, h_J\}$, and $h_j$ is used instead of h of Expression 4. At this time, when h α$n_j$ is set using the value n of the noise map and a proportionality low factor α, α can be handled similarly to h in S6-2.

(S12-4)

The second local bias component extraction unit 1104 extracts a local bias component low-frequency image from the low-frequency component image using the noise map. Although the local bias component extraction process using the noise map is similar to S12-2, the low-frequency component image has the fluctuations of the pixel value are smaller than the reconstruction image, and in the present step, the noise map is corrected for use. When the noise map the same as the reconstruction image is used for the low-frequency component image, local bias components are extracted in an excessive noise amount, and the smoothing effect is too much. Thus, correcting the noise map prevents an excessive smoothing effect.

In the following, the procedures of correcting the noise map will be described. First, the noise map is decomposed into a plurality of frequency bands. Note that the cutoff frequency used for frequency decomposition is matched with the cutoff frequency used by the low-frequency component image creating unit. Subsequently, components in the lowest frequency band of the decomposed frequency band are extracted as a corrected noise map.

From the process flow described above, the signal of a low-contrast structure included in a medical image can be extracted and enhanced, and a medical image suited to diagnosis can be present to an operator. More specifically, according to the embodiment, the signal of a low-contrast structure can be extracted highly accurately, and thus a medical image more suited to diagnosis can be present to the operator.

Fourth Embodiment

In the first embodiment, the description is made in which the operator sets the signal enhancement gain used in computing the contrast enhanced image. The operator can interactively set the signal enhancement gain on one hand, in order to reduce the number of operator operation, automatic setting of the signal enhancement gain is more desirable. Therefore, in the embodiment, the description will be made in which a medical image processing device 1 computes and sets the signal enhancement gain.

Figure 13:
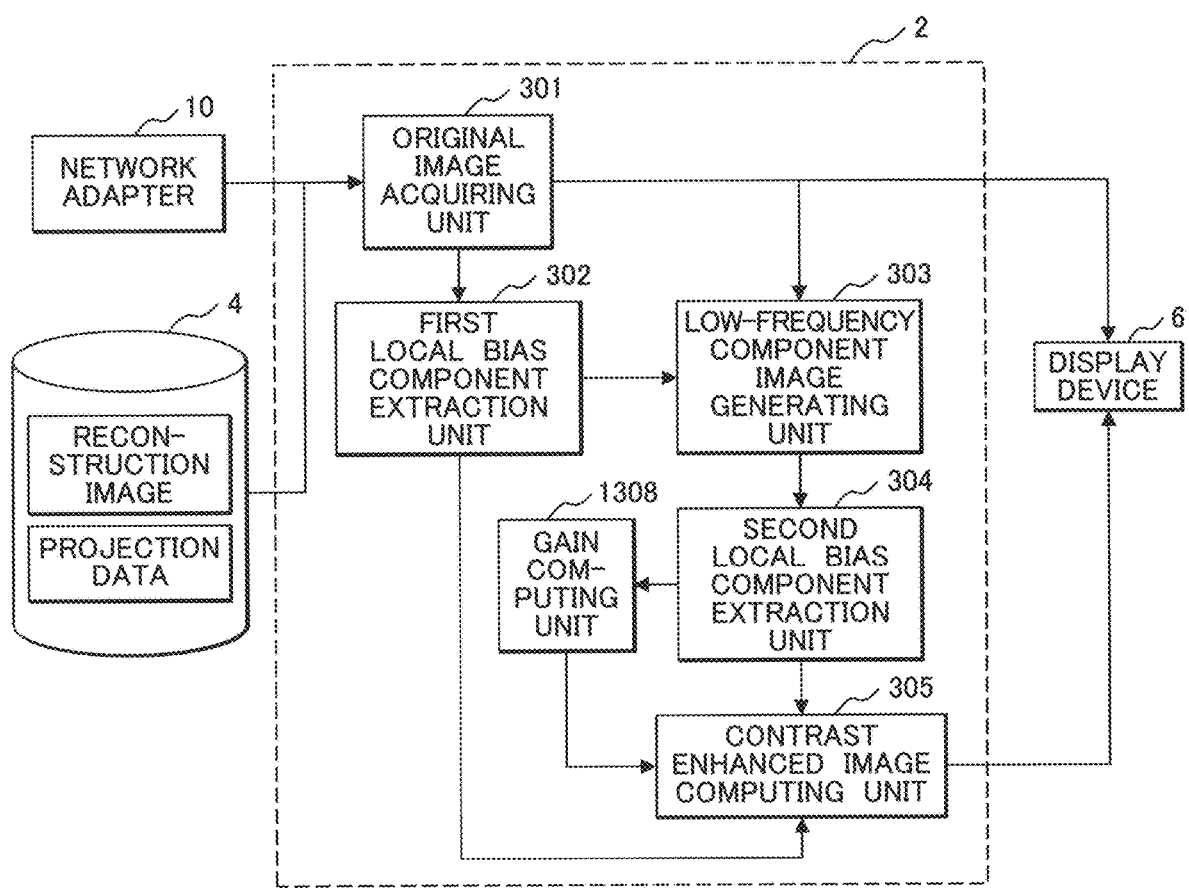
FIG. 13 is a functional block diagram of a fourth embodiment.

The main components of the embodiment will be described using FIG. 13. Since the difference between the embodiment and the first embodiment is that a gain computing unit 1308 is added, the gain computing unit 1308 will be described.

The gain computing unit 1308 computes a signal enhancement gain based on a local bias component low-frequency image. Since the local bias component low-frequency image includes information on a low-frequency component that is desired to be enhanced, the signal enhancement gain is determined based on the maximum value and minimum value of the pixel values of the local bias component low-frequency image.

Figure 14:
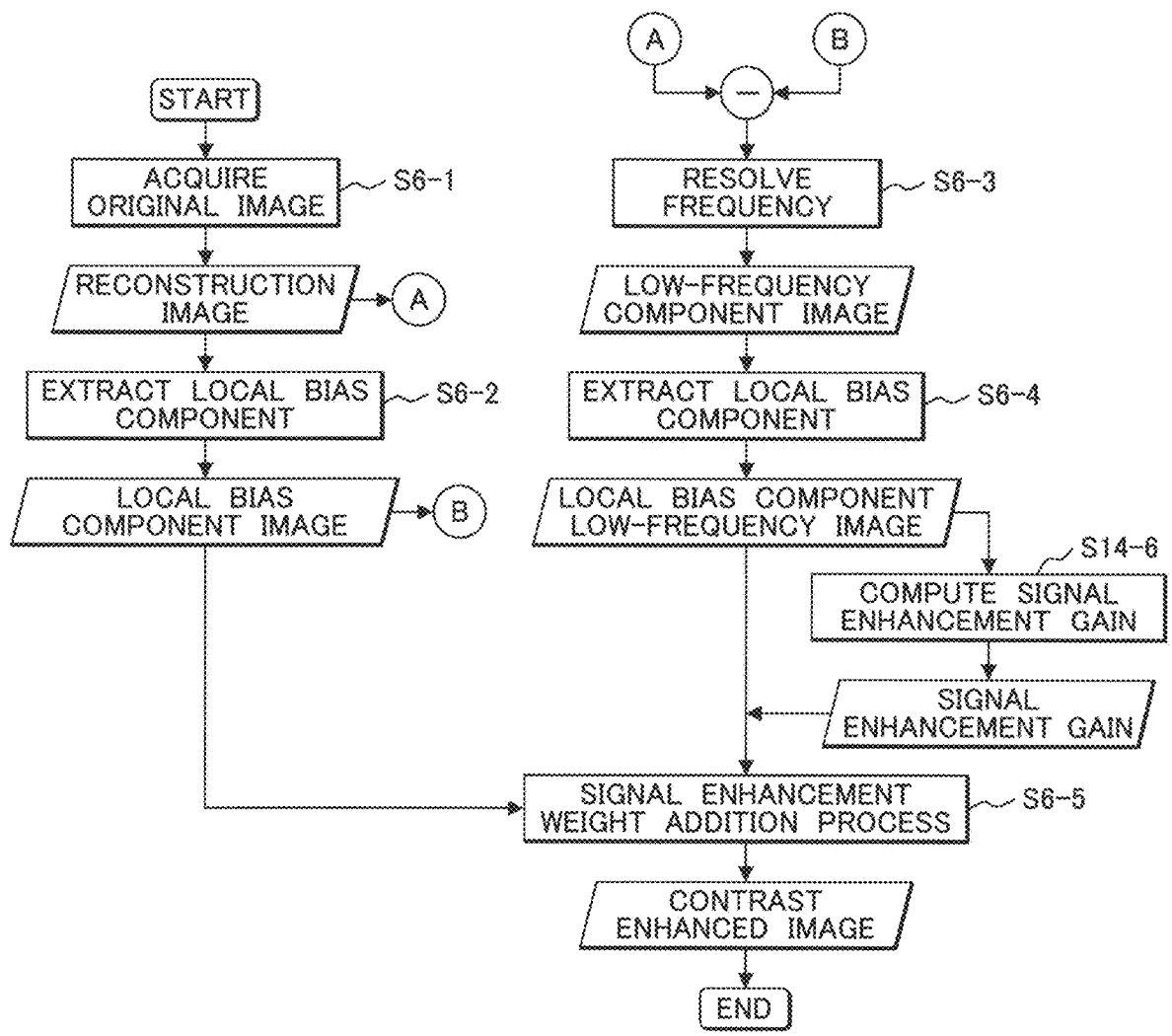
FIG. 14 is a diagram showing a process flow according to the fourth embodiment.

Referring to FIG. 14, a process flow executed by the medical image processing device 1 according to the embodiment will be described. Note that S6-1 to S6-5 in the embodiment are the same as the first embodiment, and the description is omitted.

(S14-6)

The gain computing unit 1308 computes a signal enhancement gain. A signal enhancement gain g is computed by the following expression using a maximum value M and a minimum value m of a positive value in the pixel values of a local bias component low-frequency image.

$$g = \frac{\gamma(M+m)}{2} \qquad \text{[Expression 7]}$$

here, $\gamma$ is a given parameter. The value of $\gamma$ is computed in advance such that the visibility of the low-contrast structure is the best using a phantom having a known CT value, for example, using a reconstruction image obtained by scanning the phantom shown in FIG. 4($d$) is scanned, and stored on a storage device 4. In the present step, $\gamma$ stored on the storage device 4 is read for use.

The values displayed on the minimum gain display unit 704 and the maximum gain display unit 705 in the display screen 700 shown in FIG. 7 may be $\gamma$m and $\gamma$M, respectively.

From the process flow described above, the signal of a low-contrast structure included in a medical image can be extracted and enhanced, and a medical image more suited to diagnosis can be present to the operator.

Note that the medical image processing device and the medical image processing method according to the present invention are not limited to the foregoing embodiments, and can be embodied by modifying the components in the scope not deviating from the gist of the invention. A plurality of components disclosed in the foregoing embodiments may be appropriately combined. Some of the components may be removed from all the components shown in the foregoing embodiments.

For example, the low-frequency component image creating unit 303 and the contrast enhanced image computing unit 305 according to the third embodiment and the fourth embodiment may be modified to the frequency component image creating unit 903 and the contrast enhanced image computing unit 905 according to the second embodiment. The noise map acquiring unit 1101 according to the third embodiment may be added to the fourth embodiment.

REFERENCE SIGNS LIST

1 . . . medical image processing device, 2 . . . CPU, 3 . . . main memory, 4 . . . storage device, 5 . . . display memory, 6 . . . display device, 7 . . . controller, 8 . . . input device, 10 . . . network adapter, 11 . . . system bus, 12 . . . network, 13 . . . medical imaging apparatus, 14 . . . medical image database, 100 . . . X-ray CT apparatus, 200 . . . scanner, 210 . . . examinee, 211 . . . X-ray tube, 212 . . . detector, 213 . . . collimator, 214 . . . drive unit, 215 . . . central control unit, 216 . . . X-ray control unit, 217 . . . high-voltage generating unit, 218 . . . scanner control unit, 219 . . . bed control unit, 221 . . . collimator control unit, 222 . . . preamplifier, 223 . . . A/D converter, 240 . . . bed, 300 . . . operating unit, 31 . . . reconstruction processing unit, 32 . . . image processing unit, 34 . . . storage unit, 36 . . . display unit, 38 . . . input unit, 301 . . . original image acquiring unit, 302 . . . first local bias component extraction unit, 303 . . . low-frequency component image creating unit, 304 . . . second local bias component extraction unit, 305 . . . contrast enhanced image computing unit, 700 . . . display screen, 701 . . . original image display unit, 702 . . . gain setting unit, 703 . . . selected gain display unit, 704 . . . minimum gain display unit, 705 . . . maximum gain display unit, 706 . . . contrast enhanced image display unit, 903 . . . frequency component image creating unit, 905 . . . contrast enhanced image computing unit, 1101 . . . noise map acquiring unit, 1102 . . . first local bias component extraction unit, 1104 . . . second local bias component extraction unit, 1308 . . . gain computing unit

The invention claimed is:

1. A medical image processing device that applies image processing to a medical image, the device comprising:
an acquiring unit configured to acquire an original image;
a first extraction unit configured to extract a local bias component image that is a local bias component in the original image;
a creating unit configured to decompose a difference image between the original image and the local bias component image into at least two frequency bands and create a low-frequency component image formed of a component in a lowest frequency band of the decomposed frequency band;

a second extraction unit configured to extract a local bias component low-frequency image that is a local bias component of the low-frequency component image; and a computing unit configured to multiply the local bias component low-frequency image by a gain, add to the local bias component image, and compute a contrast enhanced image.

2. The medical image processing device according to claim 1, wherein: the creating unit also creates a frequency component image formed of a component in a frequency band different from the low-frequency component image; and the computing unit multiplies the local bias component low-frequency image by a gain and adds to the local bias component image as well as the computing unit adds the frequency component image and computes a contrast enhanced image.

3. The medical image processing device according to claim 1, further comprising a noise map acquiring unit configured to acquire a noise map expressing a distribution of a noise component included in the original image, wherein the first extraction unit and the second extraction unit extract a local bias component using the noise map.

4. The medical image processing device according to claim 3, wherein the noise map acquiring unit separates projection data used in creating an original image into an even-numbered view and an odd-numbered view, and creates the noise map based on a difference image between a reconstruction image created using the even-numbered view and a reconstruction image created using the odd-numbered view.

5. The medical image processing device according to claim 1, further comprising a gain computing unit configured to compute the gain based on a pixel value of the local bias component low-frequency image.

6. The medical image processing device according to claim 1, further comprising:

a display unit configured to display the original image and the contrast enhanced image; and a gain setting unit configured to set the gain, wherein the display unit updates and displays the contrast enhanced image every time the gain is set.

7. The medical image processing device according to claim 6, wherein the gain setting unit displays a range of a settable gain.

8. The medical image processing device according to claim 7, wherein the range of the settable gain is computed based on a pixel value of the local bias component low-frequency image.

9. The medical image processing device according to claim 8, wherein the range of the settable gain is a range from a minimum value to a maximum value of a pixel value of the local bias component low-frequency image.

10. A medical image processing method of applying image processing to a medical image, the method comprising:

an acquiring step in which an original image is acquired;

a first extraction step in which a local bias component image that is a local bias component in the original image is extracted;

a creating step in which a difference image between the original image and the local bias component image is decomposed into at least two frequency bands and a low-frequency component image formed of a component in a lowest frequency band of the decomposed frequency bands is created;

a second extraction step in which a local bias component low-frequency image that is a local bias component of the low-frequency component image is extracted; and a computing step in which the local bias component low-frequency image is multiplied by a gain, added to the local bias component image, and a contrast enhanced image is computed.

* * * * *